United States Patent [19]
Takamatsu et al.

[11] Patent Number: 6,060,632
[45] Date of Patent: May 9, 2000

[54] PROCESS FOR PRODUCING ETHYLBENZENE

[75] Inventors: Yoshikazu Takamatsu; Hiroshi Ishida; Yoshihito Itani, all of Kurashiki, Japan

[73] Assignee: Asahi Kasei Kogyo Kabushiki Kaisha, Osaka, Japan

[21] Appl. No.: 09/214,845

[22] PCT Filed: Jul. 17, 1997

[86] PCT No.: PCT/JP97/02476

§ 371 Date: Jan. 14, 1999

§ 102(e) Date: Jan. 14, 1999

[87] PCT Pub. No.: WO98/03455

PCT Pub. Date: Jan. 29, 1998

[30] Foreign Application Priority Data

Jul. 19, 1996 [JP] Japan ................................. 8-207567

[51] Int. Cl.⁷ ................................. C07C 2/68; C07C 2/64
[52] U.S. Cl. ................................. 585/467; 585/446
[58] Field of Search ................................. 585/467, 446

[56] References Cited

U.S. PATENT DOCUMENTS

| | | | |
|---|---|---|---|
| 5,086,193 | 2/1992 | Sy ........................................... | 585/446 |
| 5,113,031 | 5/1992 | Sy ........................................... | 585/467 |
| 5,118,896 | 6/1992 | Steigelmann et al. ................... | 585/467 |
| 5,334,795 | 8/1994 | Chu et al. ............................... | 585/467 |

FOREIGN PATENT DOCUMENTS

| | | |
|---|---|---|
| 3-181424 | 8/1991 | Japan . |
| 4-502451 | 5/1992 | Japan . |
| 4-187647 | 7/1992 | Japan . |
| 4-266830 | 9/1992 | Japan . |
| 5-138034 | 6/1993 | Japan . |
| B2 6-43346 | 6/1994 | Japan . |
| 6-508817 | 10/1994 | Japan . |
| 8-103658 | 4/1996 | Japan . |
| 9604225 | 2/1996 | WIPO . |
| 9620148 | 7/1996 | WIPO . |

*Primary Examiner*—Walter D. Griffin
*Assistant Examiner*—Thuan D. Dang
*Attorney, Agent, or Firm*—Birch, Stewart, Kolasch & Birch, LLP

[57] ABSTRACT

A process for producing ethylated benzene by a reaction of benzene with ethylene in the presence of a catalyst containing a zeolite β by using a fixed-bed ascending-flow type reactor, which comprises a) carrying out the reaction under conditions under which ethylene bubbles are present at the inlet of a catalyst layer when ethylene is fed upward from under the catalyst layer, b) recovering reaction products as a liquid from the upper part of the reactor and at the same time taking out a distillate composed mainly of unreacted benzene therefrom as vapor, and c) adjusting the temperature of the catalyst layer at its inlet to a temperature at least 50° C. lower than the maximum attained temperature of the catalyst layer.

7 Claims, No Drawings

6,060,632

PROCESS FOR PRODUCING ETHYLBENZENE

This application is the national phase under 35 U.S.C. §371 of prior PCT International Application No. PCT/JP97/02476 which has an International filing date of Jul. 17, 1997 which designated the United States of America.

TECHNICAL FIELD

The present invention relates to a process for producing ethylbenzene useful as, for example, a starting material for various polymers.

BACKGROUND ART

WO96/20148 discloses a production process of ethylbenzene from benzene and ethylene using a zeolite such as MCM-22, MCM-49 or MCM-56 as a highly selective catalyst. According to this reference, the alkylation is carried out in a liquid phase and the benzene/ethylenemolar ratio is 5 to 10 in most cases and is 5.5 in the Examples.

U.S. Pat. No. 5,334,795 also discloses a synthetic process of ethylbenzene from benzene and ethylene using MCM-22 zeolite. However, in the Examples of this reference, the benzene/ethylene molar ratio is at least 4.6.

JP-B-06043346 discloses a process comprising bringing an organic aromatic compound into contact with a C2~C20 olefin to form alkylation products in a distillation column reactor containing a structure obtained by immobilizing a fixed-bed acidic catalyst in a packing for distillation, separating the formed alkylation products and unreacted organic aromatic compound and olefin, and taking out the alkylation products from the distillation reactor at a place under the fixed bed. This reference, however, does not disclose employment of a β zeolite. Moreover, in the Examples of the reference, the benzene/ethylene molar ratio of the reaction products recovered from the bottom is at least 3.47 and the production rate of ethylbenzene relative to the weight of the catalyst is as very low as 0.12 to 0.3.

U.S. Pat. No. 5,118,896 discloses a process in which continuous liquid-phase alkylation of a liquid aromatic compound selected from benzene, toluene and xylene using an olefin as an alkylating agent is carried out in the fixed bed of a reactive-distillation type reactor by using a catalyst comprising a crystalline aluminosilicatezeolite, silica and alumina and having a pore volume of 0.25 to 0.35 ml/g, a pore radius of more than 450 Å and aparticle diameter of not more than 1/64 inch. This reference describes an example using a reactive distillation method in which the molar ratio of the aromatic compound to ethylene is 2. In this example, the conversion of ethylene is as very low as 55%.

JP-A-04187647 discloses a process in which alkylation and transalkylation are carried out together on a molecular sieve catalyst for aromatic alkylation and transalkylation in a liquid phase, and the benzene/ethylene molar ratio is 4 or less and may be about 2. In this reference, a β zeolite is mentioned as the catalyst for alkylation and the benzene/ethylene molar ratio is 5.2 in the Examples. The reference discloses a method for attaining a benzene/ethylene molar ratio of 2 under idealized reaction conditions. However, in this method, the above molar ratio value is attained by feeding ethylene in five stages.

WO96-04225 discloses fixed-bed liquid-phase alkylation by gas-liquid descent parallel-flow method carried out in a trickle bed region by the use of a β zeolite as a catalyst. However, this process has a high productivity but is disadvantageous in that the catalytic activity is greatly changed in the initial stage of the reaction and is difficult to control.

JP-A-03181424 discloses liquid-phase alkylation and transalkylation which use a β zeolite as a catalyst, and the molar ratio of an aromatic hydrocarbon to an olefin is 4 or more in the Examples of this reference.

Zeolite catalysts are used as catalysts for alkylation of aromatic hydrocarbons and can be advantageously used as non-corrosive catalysts in place of the conventional catalysts for Friedel-Crafts reaction. Therefore, various proposals have been put forward for the zeolite catalysts.

However, in most conventional processes, alkylation is carried out at a relatively high benzene/ethylene molar ratio. Since such a high molar ratio increases the amount of unreacted benzene to be recycled and hence the trouble of benzene recovery, it is very disadvantageous from an industrial viewpoint. The reasons why alkylation is carried out at a high benzene/ethylene molar ratio in the conventional processes in spite of the above fact are the following three reasons.

The first reason is the limitation of catalytic capability, i.e., a low selectivity of nuclear ethylation. For example, Y type zeolites have been most widely used as alkylation catalysts. The Y type zeolites have been known to give a satisfactory activity and a good selectivity of a desired product but have been unusable by any means at a low benzene/ethylene molar ratio because it was found that at such a low benzene/ethylene molar ratio, the production of by-products such as butylbenzene and diphenylethane becomes remarkable with an increase of the conversion of benzene, resulting in a markedly decreased selectivity of nuclear ethylation.

The second reason is that in the reaction carried out at a low benzene/ethylene molar ratio under a relatively low pressure by one-stage feed, ethylene exists as bubbles substantially at the inlet of a catalyst layer, so that the activity of the catalyst is markedly decreased. For example, JP-A-04187647 discloses employment of a Y zeolite as a transalkylation catalyst and describes the fact that when transalkylation of diethylbenzene was carried out using the Y zeolyte catalyst in a trickle bed reactor substantially containing a gas phase, the conversion of diethylbenzene was markedly decreased in several hours to 24 hours.

As a result of investigation by the present inventors, the following was found: when benzene is ethylated by a fixed-bed ascending-flow method using a Y type zeolite, at a low benzene/ethylene molar ratio under a relatively low pressure, the selectivity of nuclear ethylation is very low and the activity is markedly decreased. It was confirmed that also in a batch reaction using a Y type zeolite, the selectivity and the activity are markedly decreased with an increase of the conversion of benzene. It is conjectured that this decrease is due to the porous structure of the Y type zeolite. That is, when there are compared the Y type zeolite and a β zeolite which have the same oxygen-containing 12-membered structure, the Y type zeolite has large cavities called supercages at the intersections of pores. It can be speculated that the production of binuclear products (e.g. diphenylethane) as by-products becomes easy in the cavities and causes the decrease of the selectivity and the clogging of the pores with high-molecular weight substances (i.e. the decrease of the activity) at the same time.

JP-A-06508817 discloses alkylation using as a catalyst a mordenite type zeolite having a silica/alumina molar ratio of more than 160 and an index of symmetry of at least 1. The alkylation is carried out in a reactor containing substantially no gas. Most preferably, it is carried out in a completely liquid phase. The reference describes the fact that the substantial presence of a gas causes accumulation of an alkylating agent in the gas to polymerize the alkylating agent, so that the decrease of the selectivity and the inactivation of the catalyst are accelerated. That is, the reference describes the impossibility of carrying out the alkylation using the above-mentioned mordenite type zeolite as a catalyst in a gas-liquid mixed phase substantially containing ethylene bubbles.

Also in the case of MCM-22, MCM-49 and MCM-56 zeolite catalysts, the highly selective catalysts disclosed in WO96/20148, etc., the benzene/ethylene molar ratio is at least 4.6 as described above and moreover this value could be attained only by multi-stage feed of ethylene to be completely dissolved. That is, for inhibiting the deterioration of the catalytic activity, the reaction can be carried out only under conditions under which ethylene is completely soluble in benzene.

For using the above-mentioned catalyst, complete dissolution of ethylene in benzene is necessary. For carrying out the reaction at a low benzene/ethylene molar ratio, multistage feed of ethylene or a high pressure for increasing the solubility would be necessary. Therefore, a higher pressure and a higher-order multi-stage feed are required for utilizing low-purity crude ethylene as a starting material, so that ethylene purification becomes indispensable. Thus, the above-mentioned catalyst is not industrially usable in practice.

The third reason is a problem of removing the heat of reaction. Since the reaction is an exothermic reaction, heat is markedly generated when the reaction is completed at a low benzene/ethylene molar ratio. The rise of the temperature of a catalyst layer caused by the heat generation lowers the selectivity of alkylation, and if a liquid phase cannot be maintained, a remarkable decrease of the catalytic activity cannot be avoided. The removal of the heat of reaction is an important problem, and in conventional processes, alkylation has been unavoidably carried out in the presence of a large excess of benzene (at a high benzene/ethylene molar ratio) also from the viewpoint of the heat removal.

In such circumstances, there has been proposed a method for solving the problem of removing the heat of reaction, in order to achieve alkylation at a low benzene/ethylene molar ratio.

JP-A-04502451 or JP-A-04187647 has proposed a method for multi-stage feed of ethylene. However, an apparatus for the multi-stage feed is complicated, and even when the multi-stage feed was conducted, alkylation is carried out at a high benzene/ethylene molar ratio of 3 or more in Examples of the reference. For example, JP-A-04502451 describes the following: benzene is fed to the first reaction zone of an alkylation reactor having at least two reaction zones and a fresh olefin is fed to the entrance of each zone to carry out alkylation, whereby the benzene/olefin molar ratio in the whole reactor is reduced while maintaining the benzene/olefin molar ratio in each zone at a sufficiently high value to prevent the temperature rise, and thus a temperature rise to an abnormal temperature is avoided, resulting in an improved selectivity and an extended life of a catalyst. The reference describes the fact that since the reaction is carried out at a low temperature, a zeolite catalyst can be held in a liquid phase, so that a time required for the regeneration of the catalyst to become necessary can be extended.

WO96/20148 discloses a process using MCM-22, MCM-49 or MCM-56 zeolite as a catalyst. According to this process, an olefin is fed in multiple stages and the heat of reaction is removed by providing one or more stages of cooling. This reference describes the fact that practice of the process at a substantially constant temperature increases the purity of the product and the life of the catalyst.

When such a process is employed, the number of stages of ethylene feed and the number of stages of cooling should be increased for attaining a lower benzene/ethylene molar ratio, resulting in a complicated apparatus.

On the other hand, there has also been proposed a process in which the heat of reaction is removed as a latent heat for evaporation by carrying out reactive distillation. For example, in the above reference JP-B-06043346, a Y type zeolite as a catalyst is wrapped in cloth and packed in the reactor. The products are recovered from the bottom of the reactor. Since the Y type zeolite catalyst is markedly deteriorated in activity in the presence of substantially gaseous ethylene, the contact between the catalyst and ethylene bubbles is avoided by the use of the cloth and it can be speculated that ethylene is in a substantially completely dissolved state in the reaction zone. However, when a Y type zeolite is used as a catalyst, it is by no means easy to carry out the reaction at a low benzene/ethylene molar ratio, also from the viewpoint of maintaining the selectivity. In practice, the lowest benzene/ethylene molar ratio of the products obtained from the bottom is at least 3.47 in the Examples of JP-B-06043346. In such a reactive distillation method, since gaseous ethylene forms a continuous phase and moreover there is employed a catalyst packing method which avoids the contact between the catalyst and ethylene bubbles, complete conversion of ethylene is considered impossible as a matter of course.

U.S. Pat. No. 5,118,896 also discloses a reactive distillation method and mentions employment of a $\beta$ zeolite as a catalyst. However, only ethylation of toluene by the use of a Y type zeolite is described in the Examples of this reference, and in the Examples using reactive distillation, the catalyst is used wrapped in cloth. Therefore, also in these Examples, ethylene bubbles are shut off from a catalyst, so that a uniform liquid phase is maintained in a reaction zone. In this case, the area of gas-liquid interface is inevitably the surface area of the cloth and hence cannot be large. Therefore, a considerable number of stages (a considerable amount of the catalyst) is necessary for completing the conversion of ethylene, so that the productivity relative to the catalyst would be low. In practice, in the Examples of the reference, the conversion of ethylene is only 55% under the following conditions; (toluene+benzene)/ethylene molar ratio: 2, catalyst weight: 272 g, feed rate of toluene: 151 g/Hr, feed rate of benzene: 27 g/Hr. In addition, carrying out the reaction by the reactive distillation method described above is dis-advantageous in that fixation of the catalyst layer in a reactor is difficult, resulting in a complicated apparatus.

The same reference U.S. Pat. No. 5,118,896 describes ethylation of toluene by the use of a Y type zeolite by a fixed-bed ascending-flow gas-liquid mixed-phase method using ethylene diluted with methane as a starting material, as an experiment for evaluating the catalyst. However, in this case, a catalyst layer is maintained at a constant temperature with a divided electric furnace. In such a reaction method, even if a $\beta$ zeolite is used as a catalyst in place of the Y type zeolite, complete conversion of ethylene cannot be achieved and the catalyst is markedly deteriorated in activity. The reason is as follows: the starting liquid components are evaporated from the inlet of the catalyst layer at a high temperature and the solubility of ethylene at the inlet of the catalyst layer is decreased, so that the reaction cannot be completed; and the higher the temperature, the more remarkable the deterioration in activity of the catalyst in the presence of gaseous ethylene. Examples of the above reference are only intended to evaluate the catalyst and no long-term operation was carried out therein. In these Examples, even short-term operation resulted in a decrease of the catalytic activity, and no complete conversion of ethylene was achieved.

As described above, in the conventional processes, the reaction is carried out in a complete dissolution system in order to prevent substantially the presence of ethylene bubbles at least in a reaction zone, in view of the capability of a catalyst (the selectivity), the decrease of activity of the catalyst, and the removal of the heat of reaction. That is, there has been no choice but to carry out the reaction at a high benzene/ethylene molar ratio.

In such circumstances, when an industrially advantageous low benzene/ethylene molar ratio is desired, the reaction should be carried out under a very high pressure, for example, for attaining the low benzene/ethylene molar ratio in one stage in a complete dissolution system. Therefore, in the conventional processes, there is no choice but to employ a method comprising multi-stage feed of ethylene. Since there is also a problem of removing the generated heat of reaction, a heat exchanger should be provided. If the heat of reaction is not removed, the temperature of a catalyst layer is raised, so that the solubility of ethylene would be further decreased. For carrying out the reaction in a complete dissolution system, starting ethylene is required to have a high purity and hence ethylene purification is absolutely necessary. This is because a higher pressure is required for using diluted ethylene as a starting material.

On the other hand, there have often been proposed so-called reactive-distillation type reactors in which latent heat of evaporation is utilized for removing the heat of reaction. However, also in the actual reaction zone of such a reactor, ethylene should be completely dissolved and avoidance of the contact between a catalyst and ethylene bubbles is important, resulting in a complicated apparatus and a complicated method for packing the catalyst. Moreover, since complete conversion of ethylene is impossible in principle, a finishing reactor is necessary for converting the residual ethylene as much as possible. Such demands on an apparatus pose an important problem in industrial production.

DISCLOSURE OF THE INVENTION

The present inventors earnestly investigated in order to solve the problems described above, and consequently found that when there is employed a process for producing ethylbenzene from benzene and ethylene in the presence of a catalyst containing a zeolite β by using a fixed-bed ascending-flow type reactor, wherein
 a) the reaction is carried out under conditions under which ethylene bubbles are present at the inlet of a catalyst layer when ethylene is fed upward from under a catalyst layer,
 b) simultaneously with the recovery of the reaction products as a liquid from the upper part of the reactor, a distillate composed mainly of unreacted benzene is taken out therefrom as vapor, and
 c) the temperature of the catalyst layer at its inlet is adjusted to a temperature at least 50° C. lower than the maximum attained temperature of the catalyst layer,
it becomes possible even at a very low benzene/ethylene molar ratio to remove the generated heat of reaction easily and suppress the abnormal rise of the temperature of the catalyst layer, so that ethylated benzene can be produced in very high yield with high selectivity. On the basis of the above finding, the present invention has been accomplished. According to the present invention, ethylene can be completely converted, the decrease in activity of the catalyst can be suppressed, and the reaction can be carried out at a low benzene/ethylene molar ratio under a low pressure by the use of a simple apparatus.

The present invention is a process for producing ethylbenzene from benzene and ethylene in the presence of a catalyst containing zeolite β by using a fixed-bed ascending-flow type reactor, wherein
 a) the reaction is carried out under conditions under which ethylene bubbles are present at the inlet of a catalyst layer when ethylene is fed upward from under the catalyst layer,
 b) simultaneously with the recovery of the reaction products as a liquid from the upper part of the reactor, a distillate composed mainly of unreacted benzene is taken out therefrom as vapor, and
 c) the temperature of the catalyst layer at its inlet is adjusted to a temperature at least 50° C. lower than the maximum attained temperature of the catalyst layer.

BEST MODE FOR CARRYING OUT THE INVENTION

The catalyst used in the present invention is a zeolite β. Zeolites β are synthetic crystalline aluminosilicates disclosed for the first time in U.S. Pat. No. 3,308,069 and are identified by their characteristic X-ray diffraction patterns described in this reference. Table 1 shows reflection d values obtained for the zeolites β in X-ray diffraction.

TABLE 1

| Reflection d values for β zeolites |
| --- |
| 11.4 ± 0.2 Å |
| 7.4 ± 0.2 |
| 6.7 ± 0.2 |
| 4.25 ± 0.1 |
| 3.97 ± 0.1 |
| 3.0 ± 0.1 |
| 2.2 ± 0.1 |

The $SiO_2/Al_2O_3$ ratio of the zeolite β used in the present invention is 5 to 100, preferably 10 to 80, more preferably 15 to 40.

The zeolite β used as a catalyst in the present invention is preferably so-called acid type zeolite β obtained by replacing sodium ions by hydrogen ions and/or polyvalent cations by ion exchange. A zeolite β having a sufficient organic cations/sodium ions ratio can be used after only calcination. For attaining a higher activity, it is preferable to convert a zeolite β to a hydrogen ion type by ion exchange. The ion exchange into the hydrogen ion type is preferably carried out by the following method.

A synthesized zeolite β is calcined to be freed of organic substances, and then stirred in a dilute aqueous nitric acid solution to be subjected to ion exchange into a hydrogen ion type, which is dried to be freed of water so that the amount of water contained therein may be 10 parts by weight or less, and the dried product is used for the reaction.

In packing the catalyst into the reactor, the catalyst is preferably a shaped or molded article. For obtaining the shaped or molded article, there may be shaped or molded either a pure zeolite or a zeolite containing one or more inorganic oxides (e.g. alumina, silica, silica/alumina or natural clay) as a binder(s). As a shaping or molding method, tableting, extrusion, etc. are well known in the art. The shape of the shaped or molded catalyst is generally cylindrical. For example, spherical, plate-like or hollow-and-cylindrical shaped or molded articles are also used.

The mode of reaction in the present invention is a fixed-bed ascending-flow reaction mode. The catalyst shaped or molded product is packed into the reactor. Benzene, a reactive material is introduced into the reactor through the lower part of the reactor after being preheated to a predetermined temperature 50° C. lower than the maximum attained temperature of the catalyst layer. On the other hand, ethylene is also introduced into the lower part of the reactor or the catalyst layer. Since the reactor is heat-insulating and the reaction is exothermic, heat is generated as the reaction proceeds, so that the liquid temperature (the temperature of the catalyst layer) rises. However, since the operating pressure is low in the present invention, evaporation is inevitably caused at a gas-liquid equilibrium composition under conditions of temperature and pressure given in individual cases. The evaporation gas becomes a distillate composed mainly of benzene and the volume of the gas is determined by the balance between the quantity of the generated heat of reaction and the quantity of heat removed as the sensible heat of the liquid, depending on the reaction conditions such as the reaction pressure, the feed rates of the starting materials, the heat of reaction, the preheating temperature of the starting materials, etc. Therefore, the maximum attained temperature of the catalyst layer can be controlled to be an arbitrary constant temperature by removing some of the large heat of reaction generated with the progress of alkylation, as the latent heat for evaporation to suppress the rise of the reaction temperature. This control is effective in suppressing the deterioration of the catalyst and maintaining the selectivity.

The reactive materials in the present invention are benzene and ethylene used as an alkylating agent. The distillate composed mainly of unreacted benzene which is recovered as vapor in order to remove the heat of reaction can be reused as a reactive material.

Benzene used as starting material in the present invention is preferably freed of water to have a water content of 200 ppm or less for the purpose of preventing a decrease of the catalytic activity caused by the adsorption of water on the catalyst in a low temperature region.

As ethylene used as starting material in the present invention, there can be used not only purified ethylene gas but also crude ethylene gas (containing, for example, paraffin hydrocarbon gases such as methane and ethane, propylene, and hydrogen) produced in a conventional naphtha cracker.

The process of the present invention is characterized in that the reaction can be carried out in a gas-liquid mixed phase. Therefore, the reaction can be carried out under a relatively low pressure also when the crude ethylene gas is used as starting material. On the other hand, a process requiring complete dissolution of ethylene in benzene as before is not practical because a very high pressure is necessary for dissolving ethylene when starting crude ethylene gas is used. Accordingly, the process of the present invention is desirable from an industrial viewpoint because a step of purifying starting ethylene can be omitted.

The benzene/ethylene molar ratio of a reactive gas fed in the present invention (hereinafter referred to as "benzene/ethylene feeding molar ratio" or merely as "feeding molar ratio") is 1 to 6, preferably 1.5 to 4, more preferably 2 to 3.

In the present invention, since a portion of unreacted benzene is recovered as vapor, the product solution has a benzene ring/ethyl group molar ratio lower than the feeding molar ratio. When the evaporation gas distillate is reused by recycling and feeding the gas to the reactor as described above, there can be obtained a product solution having the same benzene ring/ethyl group molar ratio as the feeding molar ratio. The benzene ring/ethyl group molar ratio of the product solution is preferably 1 to 3 for maintaining a high selectivity. Therefore, when the evaporation gas distillate is reused by recycling and feeding the gas to the reactor, the adjustment of the benzene/ethylene feeding molar ratio of the reactive gas to be fed to 1 to 3 is sufficient to attain a benzene ring/ethyl group molar ratio of the product solution of 1 to 3.

The reaction pressure in the present invention is determined by the partial pressure of the evaporation gas composed mainly of benzene which is determined by gas-liquid equilibrium, depending on the composition of a desired product solution, the benzene/ethylene feeding molar ratio, the maximum attained temperature of the catalyst layer, etc. It is usually preferable to adjust the maximum attained temperature of the catalyst layer (i.e. the gas-liquid equilibrium temperature) to 250° C. or lower for maintaining the selectivity of nuclear ethylation. The pressure is determined so that boiling may occur at 250° C. or lower to cause concentration of the product solution. When the reaction pressure is too low, it is feared that the reaction rate is decreased and that the degree of evaporation, i.e., the degree of recycling is increased. Therefore, as to a preferable pressure, the partial pressure of the produced vapor distillate composed mainly of benzene is 5 to 20 kg/cm$^2$G, preferably 10 to 15 kg/cm$^2$G for attaining a sufficient reaction rate and keeping the composition and flow rate of the product solution to be recovered and the composition and the flow rate of the vapor to be recycled, in practical ranges.

When crude ethylene is used as starting material, gas components other than the olefin component such as ethylene or propylene, which is consumed in the alkylation are discharged into the gas phase together with the vapor distillate composed mainly of benzene. Therefore, for establishing the same evaporation gas-liquid equilibrium as in the case of using pure ethylene, the reaction is carried out at an operating pressure corrected for the partial pressure. The operating pressure should be determined by considering the purity of ethylene.

The reaction temperature in the present invention is defined as the maximum attained temperature of the catalyst layer. It is determined by the reaction pressure and the composition of the liquid and is preferably 170–250° C. for maintaining sufficient reaction rate and selectivity. The reaction pressure is properly chosen as described above so that the reaction temperature may fall in the above range. Therefore, the reaction temperature is raised to a desired temperature by the heat of reaction. However, since the whole of the residual heat of reaction is used for evaporating the distillate composed mainly of benzene, the temperature of the catalyst layer can be kept constant.

In the present invention, the temperature of the catalyst layer at its inlet (the benzene preheating temperature) is set at a temperature at least 50° C. lower than the above-mentioned maximum attained temperature of the catalyst layer. The reason is as follows: keeping the temperature of the catalyst layer at the inlet low increases the solubility of ethylene at the inlet of the catalyst layer and hence contributes greatly to the complete conversion of ethylene; and it gives a temperature profile of the catalyst layer from the temperature at the inlet to the maximum attained temperature, i.e., the boiling point attained under predetermined conditions, so as to further lower the average temperature of the catalyst layer, and hence it is effective in maintaining a high selectivity. Since the decrease of the catalytic activity in the vicinity of the inlet of the catalyst layer where ethylene bubbles are substantially present is dependent on temperature, the temperature of the catalyst layer at its inlet is preferably as low as possible also from the viewpoint of preventing the decrease of the activity. The actual preheating temperature (the temperature of the catalyst layer at its inlet) in the present invention is determined in view of the composition of a desired product solution (the volume of the evaporation gas). As a temperature at which the reaction is initiated, the actual preheating temperature is 30° C. or higher and chosen so as to be 50° C. or more lower than the maximum attained temperature of the catalyst layer, and it is preferably 30–200° C., more preferably 80–160° C.

Thus, in the present invention, the temperature of the catalyst layer is lowest at the inlet of the catalyst layer and rises with a decrease of the distance to the top of the catalyst layer owing to heat generation caused by the progress of the reaction. When the temperature reaches a predetermined temperature, evaporation takes place and the heat of reaction is removed as the latent heat of evaporation, so that the temperature does not rise any more. Since the catalyst layer has a predetermined temperature profile, keeping the temperature of the catalyst layer at the inlet low increases the solubility of ethylene at the inlet of the catalyst layer and hence contributes to the increase of the reaction rate and the complete conversion of ethylene. According to the present invention, even if ethylene bubbles are present at the inlet of the catalyst layer, an effect of suppressing the decrease of the catalytic activity can be obtained by keeping said layer at a low temperature. Such a temperature profile of the catalyst layer means a lowering of the average temperature of the whole catalyst layer, and this lowering is effective in maintaining the selectivity of nuclear ethylation at a very high value.

Under the conditions of a low benzene/ethylene feeding molar ratio and a low pressure which are employed in the present invention, ethylene fed cannot, as a matter of course, be completely dissolved in benzene at the inlet of the catalyst layer and is present as bubbles. Conventional processes involve, for example, the following problems: in the above situation, the deterioration of the catalyst and the decrease of the selectivity become remarkable and the temperature is raised by the large heat of reaction. In the conventional processes, for avoiding these problems, the reaction is carried out at a high benzene/ethylene molar ratio at which ethylene is completely dissolved in benzene, and for obtaining a product having a low benzene ring/ethyl group molar ratio, there is no choice but to adopt a very troublesome reaction method. However, surprisingly, according to the present invention, the alkylation at a low benzene/ethylene molar ratio can be carried out with a very simple apparatus under a low pressure. Therefore, the alkylation can be carried out even by using starting ethylene of low purity, so that an ethylene purification step can be omitted.

The present inventors found for the first time that a β zeolite is excellent in resistance to deterioration caused by its contact with gaseous ethylene and can exhibit a high catalytic activity and a high reaction selectivity even at a low benzene/ethylene molar ratio. On the basis of this finding, the inventors made it possible to maintain the temperature of a catalyst layer at an arbitrary temperature by using the β zeolite as catalyst and removing some of the generated heat of reaction by evaporating a distillate composed mainly of unreacted benzene. Thus, the inventors found a process which permits completion of the alkylation (complete conversion of ethylene) with high selectivity even at a low benzene/ethylene molar ratio. Furthermore, in the process of the present invention, the decrease in activity of the catalyst is very slight.

The present invention is explained with reference to examples. The present invention is not limited to the examples and various alternations and modifications can be made within the scope of gist of the invention.

EXAMPLE 1

Synthesis of a β Zeolite

160 Grams of a 10% aqueous tetraethylammonium hydroxide solution, 140 g of water, 4.2 g of sodium hydroxide and 9.5 g of sodium aluminate NaAlO2 were mixed to effect dissolution, followed by adding thereto 70.5 g of fused silica "Nipsil" (a trade name of NV-3, mfd. by Nippon Silica Industrial Co., Ltd.) and 7 g of a β zeolite as a seed crystal, and the resulting mixture was stirred for 30 minutes in a homogenizer at a rate of 5,000 rotations per minute. Then, the mixture was placed in a 500-ml autoclave and allowed to stand at 155° C. for 8 days without stirring to give a large amount of a crystalline substance. This substance was filtered, washed with water and then dried at 120° C. for 24 hours to obtain 66 g of crystalline powder. Subsequently, the crystalline powder was slowly heated to 350–550° C. and finally calcined at 550° C. for 6 hours. The calcined powder was confirmed to be β zeolite by X-ray diffraction.

Hydrogen Ion Exchange of the β Zeolite

To 450 g of a 0.15N aqueous nitric acid solution was added 50 g of the calcined β zeolite, and the resulting mixture was stirred at room temperature for 3 hours to carry out ion exchange. After the exchange, the exchange product was filtered, washed with water and then dried at 120° C. to obtain hydrogen ion type β zeolite. The composition of this zeolite was analyzed with a X-ray microanalyzer (EPMA). The silica/alumina ratio was 25. Synthesis and hydrogen ion exchange of zeolite were carried out several times by the same procedures as described above. Some of the thus obtained hydrogen ion type β zeolite was shaped into tablets of 3 mmφ×3–5 mmL with a tablet machine. By repeating the same procedure as described above, 400 g of shaped catalyst was obtained.

Alkylation Experiment

400 Grams of the above-mentioned shaped product of zeolite β catalyst was packed into a stainless-steel reaction tube with an inside diameter of 42.8 mm and a length of 1,500 mm equipped with a heating medium jacket as a preheating layer around the lower region of the reactor from the bottom to a height of 600 mm, a pressure control valve at the outlet of the reactor, and an overflow nozzle for taking out a product solution which was located below the pressure control valve. The catalyst packing region was a region between heights of 600 mm and 1,320 mm from the bottom of the reactor, and a stainless-steel Dickson packing of 3 mmφ was packed over and under the catalyst layer. The nozzle for taking out a product solution was connected to a solution recovery drum which had been pressurized with nitrogen so as to be equal to the reactor in internal pressure. At the outlet of the reactor, an evaporation gas distillate was recovered from the pressure control valve through a condenser, and the liquid was recovered as a product solution into the solution recovery drum through the nozzle for taking out a product solution.

Benzene was fed at a feed rate of 2,280 g/Hr through the bottom of the reactor (the inlet of the preheating layer). The internal pressure of the reactor was adjusted to 13.8 kg/cm2G with the pressure control valve at the outlet of the reactor to make the inside of the system completely liquid-sealed. A heating medium kept at 150° C. was circulated in the heating medium jacket provided as preheating layer, to adjust the temperature of the catalyst layer at its inlet to 122° C. Then, like benzene, ethylene was fed through the bottom of the reactor at a feed rate of 10.18 mol/Hr to initiate the reaction. After the initiation of the reaction, the temperature of the catalyst layer rose slowly and the maximum attained temperature of the catalyst layer reached 230° C. in the middle region of the catalyst layer. Since partial evaporation was caused under the reaction conditions employed in the present example, a further temperature rise was inhibited and the temperature of 230° C. was maintained also in the upper part of the catalyst layer. The temperature at the overflow nozzle position (the liquid level position) was 222° C. The benzene/ethylene feeding molar ratio was 2.87. It was clear that under such conditions, the ethylene fed could not be completely dissolved in benzene, so that ethylene bubbles were present at the inlet of the catalyst layer.

The product solution was obtained at a rate of 1,572 g/Hr in such a concentrated state that its benzene ring/ethyl group molar ratio was 2.14. The selectivity of nuclear ethylation products was 99.7%. The evaporation gas distillate was obtained at a rate of 992 g/Hr and had a benzene ring/ethyl group molar ratio of 6.06. The conversion of ethylene was 99.97%, namely, ethylene was substantially completely converted. The reaction was continued for 500 hours. Based on the tendency of change of the temperature profile of the catalyst layer (in particular, the temperature change near the inlet of the catalyst layer), the decrease of the catalytic activity was found to proceed slowly. The conversion of ethylene, however, did not show at all a tendency of decreases, namely, substantially complete conversion was achieved. The results obtained are shown in Table 2.

TABLE 2

| Operation time (Hr) | 50 | 100 | 500 |
|---|---|---|---|
| Temperature (° C.) | | | |
| Inlet of catalyst layer | 122 | 121 | 122 |
| Maximum attained temperature of catalyst layer | 230 | 230 | 230 |
| Position of nozzle for taking out product solution | 222 | 222 | 222 |
| Reaction pressure (kg/cm²G) | 13.81 | 13.82 | 13.81 |
| Feed of materials (mol/Hr) | | | |
| Benzene | 29.23 | 29.23 | 29.23 |
| Ethylene | 10.18 | 10.18 | 10.18 |
| Feeding molar ratio benzene/ethylene | 2.87 | 2.87 | 2.87 |
| Product solution | | | |
| Recovery rate (g/Hr) | 1572 | 1577 | 1574 |
| Composition (wt %) | | | |
| Benzene | 53.12 | 53.06 | 53.06 |
| Ethylbenzene | 34.88 | 35.01 | 35.11 |
| Diethylbenzene | 10.16 | 10.07 | 10.09 |
| Triethylbenzene | 1.64 | 1.69 | 1.58 |
| Benzene ring/ethyl group | 2.14 | 2.14 | 2.14 |
| Selectivity of nuclear ethylation | 99.72 | 99.75 | 99.75 |
| Evaporation gas | | | |
| Recovery rate (g/Hr) | 992 | 989 | 991 |
| Composition (wt/%) | | | |
| Benzene | 80.06 | 80.10 | 80.12 |
| Ethylbenzene | 17.94 | 17.92 | 17.90 |
| Diethylbenzene | 1.84 | 1.83 | 1.82 |
| Triethylbenzene | 0.14 | 0.14 | 0.14 |
| Benzene ring/ethyl group | 6.06 | 6.08 | 6.09 |
| Selectivity of nuclear ethylation | 99.94 | 99.92 | 99.94 |
| Conversion of ethylene (%) | 100.00 | 99.96 | 99.96 |

From the present example, the following can be seen: according to the process of the present invention, the alkylation at a low benzene/ethylene molar ratio is completed with high selectivity even if ethylene bubbles are clearly present at the inlet of the catalyst layer; the heat of reaction can be removed because a portion of unreacted benzene is recovered as vapor; there can be obtained a product having a benzene/ethyl group molar ratio of as very low as about 2; and the decrease in activity of the catalyst is very slight. In the present example, the production rate (in terms of ethylbenzene) relative to the weight of the catalyst was 2.7 g-ethylbenzene/g-catalyst/hour.

EXAMPLE 2

A β zeolite (sodium type) mfd. by PQ Corporation was converted to a hydrogen ion type under the same conditions as in Example 1 to obtain hydrogen ion type β zeolite. The silica/alumina ratio of the hydrogen ion type β zeolite obtained was 35.

The hydrogen ion type β zeolite obtained was shaped into tablets of 3 mmφ×3–5 mmL with a tablet machine. The same procedure as described above was repeated to obtain 400 g of shaped catalyst.

The same reactor as in Example 1 was packed with 400 g of the catalyst. The height of the packing layer was 725 mm. Benzene was fed at a feed rate of 2,400 g/Hr through the bottom of the reactor (the inlet of the preheating layer). The internal pressure of the reactor was adjusted to 13.8 kg/cm²G with the pressure control valve at the outlet of the reactor to make the inside of the system completely liquid-sealed. A heating medium kept at 160° C. was circulated in the heating medium jacket provided as preheating layer, to adjust the temperature of the catalyst layer at its inlet to 133° C. Then, like benzene, ethylene was fed through the bottom of the reactor at a feed rate of 10.71 mol/Hr to initiate the reaction. After the initiation of the reaction, the temperature of the catalyst layer rose slowly and the maximum attained temperature of the catalyst layer reached 232° C. in the middle region of the catalyst layer. It was clear that at such a temperature and a pressure, a portion of the reaction solution was evaporated in the reactor. The evaporation gas distillate was introduced into the recovery drum containing benzene previously placed therein. The level in the drum is controlled to be constant and the liquid introduced into the drum was recycled to a starting-material line (a feed materials mixing tank) with a pump. On the other hand, benzene was fed to said tank so that the total volume of liquids fed to the reactor might be constant, namely, the liquid level in the feed materials mixing tank might be kept constant.

After several hours, the system became stable and the recycling flow rate, the benzene feed flow rate and the product solution recovery flow rate became substantially constant values of 1,042 g/Hr, 1,362 g/Hr and 1,662 g/Hr, respectively. In this case, the maximum temperature of the catalyst layer was 232° C., its temperature at the product recovery nozzle was 230° C., and the reaction pressure was 13.8 kg/cm2G. The reaction was continuously carried out for 500 hours. The results obtained are shown in Table 3.

TABLE 3

| Operation time (Hr) | 100 | 309 | 500 |
|---|---|---|---|
| Temperature (° C.) | | | |
| Inlet of catalyst layer | 131 | 133 | 131 |
| Maximum attained temperature of catalyst layer | 232 | 232 | 231 |
| Position of nozzle for taking out product solution | 230 | 230 | 230 |
|  | 230 | 230 | 230 |
| Reaction pressure (kg/cm$^2$G) | 13.81 | 13.81 | 13.81 |
| Feed of materials (mol/Hr) | | | |
| Feeding molar ratio | | | |
| Benzene | 17.46 | 17.46 | 17.46 |
| Ethylene | 10.71 | 10.71 | 10.71 |
| Benzene/ethylene | 1.63 | 1.63 | 1.63 |
| Recycling | | | |
| Flow rate of liquid (g/Hr) | 1042 | 1028 | 1044 |
| Benzene ring/ethyl group | 4.10 | 4.09 | 4.11 |
| Product solution | | | |
| Recovery rate (g/Hr) | 1661 | 1676 | 1659 |
| Composition (wt %) | | | |
| Benzene | 41.10 | 41.22 | 41.10 |
| Ethylbenzene | 43.33 | 43.30 | 43.28 |
| Diethylbenzene | 13.11 | 13.01 | 13.21 |
| Triethylbenzene | 2.00 | 2.04 | 1.99 |
| Others* | 0.45 | 0.42 | 0.43 |
| Benzene ring/ethyl group | 1.62 | 1.63 | 1.63 |
| Selectivity of nuclear ethylation | 99.57 | 99.61 | 99.61 |
| Conversion of ethylene (%) | 99.96 | 99.96 | 99.94 |

*Others: tetraethylbenzene, butylbenzene, diphenylethane, etc.

In the present example, the benzene/ethylene feeding molar ratio under steady state conditions was 1.63, the benzene ring/ethylene molar ratio was 2.78 even when the recycled liquid was added, and ethylene bubbles were clearly present at the inlet of the catalyst layer. A product solution having a benzene ring/ethyl group molar ratio of 1.62 was obtained over 500 hours. Thus, it can be seen that ethylene was substantially completely converted. The production rate (in terms of ethylbenzene) relative to the weight of the catalyst was 2.84 g-ethylbenzene/g-catalyst/hour. Furthermore, during the production, the selectivity of nuclear ethylation in the case of the product solution was maintained at a very high value of 99.6%.

EXAMPLE 3

Reaction,was carried out using the following mixed gas as starting ethylene (percents are by volume):

| Ethylene | 44.19% |
|---|---|
| Methane | 35.32% |
| Ethane | 4.44% |
| Propylene | 0.04% |
| Hydrogen | 15.94% |
| Carbon monoxide | 0.07% |

The same zeolite β catalyst shaped product and reaction apparatus as in Example 2 were used. However, in the present example, since the starting material contained inert gases such as methane and hydrogen, a gas phase pressure equalization line was provided in a gas phase recovering receiver and a product solution recovering receiver and these receivers were equalized in internal pressure.

Benzene was fed at a feed rate of 2,400 g/Hr through the bottom of the reactor (the inlet of the preheating layer). The internal pressure of the reactor was adjusted to 30.2 kg/cm2G with the pressure control valve at the outlet of the reactor to make the inside of the system completely liquid-sealed. At the operating pressure in the present example, the inert gases (hydrogen, methane, ethane and a slight volume of carbon monoxide gas) were exhausted to the gas phase recovery side. Therefore, for evaporating a starting mixed gas containing the same components in the same proportions as in Example 2, it was necessary to correct the total pressure in view of the partial pressures of the inert gases. Accordingly, the operating pressure was adjusted to 30.2 kg/cm$^2$G.

A heating medium kept at 160° C. was circulated in the heating medium jacket provided as preheating layer, to adjust the temperature of the catalyst layer at its inlet to 132° C. Then, like benzene, the starting mixed gas containing ethylene was fed through the bottom of the reactor at a feed rate of 24.25 mol/Hr (10.71 mol/Hr in terms of ethylene) to initiate the reaction. After the initiation of the reaction, the material feed rates were controlled in the same manner as in Example 2, and the system assumed a steady state after several hours. The recycling flow rate, the benzene feed flow rate and the product solution recovery rate became substantially constant values of 1,043 g/Hr. 1,362 g/Hr and 1,662 g/Hr, respectively. The reaction was continuously carried out for 500 hours. The results obtained are shown in Table 4.

TABLE 4

| Operation time (Hr) | 300 | 500 |
|---|---|---|
| Temperature (° C.) | | |
| Inlet of catalyst layer | 131 | 131 |
| Maximum attained temperature of catalyst layer | 230 | 230 |
| Position of nozzle for taking out product solution | 230 | 230 |
| Reaction pressure (kg/cm$^2$G) | 30.15 | 30.14 |
| Feed of materials (mol/Hr) Feeding molar ratio | | |
| Benzene | 17.46 | 17.46 |
| Feed rate of the whole gas | 24.25 | 24.25 |
| Ethylene | 10.71 | 10.71 |
| Benzene/ethylene | 1.63 | 1.63 |
| Recycling | | |
| Flow rate of liquid | 1033 | 1030 |
| Benzene ring/ethyl group | 4.10 | 4.09 |
| Product solution | | |
| Recovery rate (g/Hr) | 1663 | 1666 |
| Composition (wt %) | | |
| Benzene | 41.07 | 41.06 |
| Ethylbenzene | 43.32 | 43.36 |
| Diethylbenzene | 13.15 | 13.12 |
| Triethylbenzene | 2.00 | 2.00 |
| Others* | 0.47 | 0.46 |
| Benzene ring/ethyl group | 1.62 | 1.62 |
| Selectivity of nuclear ethylation | 99.53 | 99.53 |
| Convention of ethylene (%) | 99.96 | 99.94 |

*Others: tetraethylbenzene, cumene, butylbenzene, diphenylethane, etc.

From the present example, the following can be seen: in 500 hours, ethylene was completely converted, the benzene ring/ethyl group ratio of the product solution was maintained at 1.62, and the selectivity of nuclear ethylation was maintained at 99.5% for the product solution. In this case, the production rate (in terms of ethylbenzene) relative to the weight of the catalyst was 2.84 g-ethylbenzene/g-catalyst/hour. From the present example, it can also be seen that the alkylation can be carried out using starting ethylene of low purity because ethylene need not be completely dissolved unlike in conventional processes.

Comparative Example 1

This comparative example was carried out for comparing reaction results obtained by using each of a Y type zeolite and a zeolite β catalyst.

Stainless-steel reaction tube with an inside diameter of 22.1 mm and a length of 800 mm equipped with a heating medium jacket as a preheating layer around the lower region of the reactor from the bottom to a height of 300 mm and a pressure control valve at the outlet of the reactor, was packed with 30 g of particles which had been prepared by grounding a shaped product of hydrogen ion type zeolite β catalyst obtained in the same manner as in Example 1, followed by classification and particle size regulation to 8 to 14 mesh. The catalyst packing region was a region between heights of 320 mm and 510 mm from the bottom of the reactor, and a stainless-steel Dickson packing of 3 mmφ was packed over and under the catalyst layer. Benzene was fed at a feed rate of 319 g/Hr through the bottom of the reactor (the inlet of the preheating layer). The internal pressure of the reactor was adjusted to 13.5 kg/cm$^2$G with the pressure control valve at the outlet of the reactor to make the inside of the system completely liquid-sealed. A heating medium kept at 140° C. was circulated in the heating medium jacket provided as preheating layer, to adjust the temperature of the catalyst layer at its inlet to 135° C. Then, like benzene, ethylene was fed through the bottom of the reactor at a feed rate of 1.4 mol/Hr to initiate the reaction. The maximum attained temperature of the catalyst layer reached 232° C. in the middle region of the catalyst layer, but since partial evaporation was caused under the reaction conditions employed in the present comparative example, a further temperature rise was inhibited and the temperature of 232° C. was maintained also in the upper part of the catalyst layer. A condenser was provided at the outlet of the reactor and the whole products were recovered as a liquid, which was analyzed by a gas chromatography.

Next, the same experiment as above was carried out except for using a shaped product of 8 to 14 mesh of Y type zeolite LZY-82 (a trade name, mfd. by Linde Zeolite Co.) as a catalyst. The amount of the catalyst packed was 33.3 g and the catalyst layer region was a region between heights of 320 mm and 470 mm from the bottom of the reactor. The temperature of the catalyst layer at its inlet was adjusted to 145° C. and the reaction was initiated. Table 5 shows the comparison of the reaction results obtained by using each of the Y type catalyst and the β type catalyst.

TABLE 5

| Catalyst | H-β | | | LZY-82 | |
|---|---|---|---|---|---|
| Packing amount (g) | 30 | | | 33.33 | |
| Feed of materials | | | | | |
| Benzene | 4.09 | | | 4.09 | |
| Ethylene (mol/H) | 1.41 | | | 1.38 | |
| BZ/EY molar ratio | 2.91 | | | 2.96 | |
| Reaction time (Hr) | 3 | 15 | 30 | 1 | 4 |
| Temperature | | | | | |
| Inlet of catalyst layer | 135 | 135 | 135 | 145 | 145 |

TABLE 5-continued

| Exit end of catalyst layer (° C.) | 232 | 232 | 232 | 206 | 199 |
|---|---|---|---|---|---|
| Composition of solution (wt %) | | | | | |
| Benzene | 63.1 | 63.1 | 63.1 | 76.6 | 79.4 |
| Ethylbenzene | 29.3 | 29.3 | 29.3 | 18.2 | 15.5 |
| Diethylbenzene | 6.5 | 6.5 | 6.5 | 3.0 | 2.7 |
| Triethylbenzene | 0.9 | 0.9 | 0.9 | 0.7 | 0.7 |
| Others* | 0.2 | 0.2 | 0.2 | 1.5 | 1.7 |
| Benzene ring/ethyl group molar ratio | 2.91 | 2.91 | 2.91 | 4.78 | 5.38 |
| Selectivity of nuclear ethylation (%) | 99.68 | 99.68 | 99.68 | 95.42 | 93.87 |
| Conversion of ethylene (%) | 99.26 | 99.22 | 99.54 | 73.0 | 60.2 |

*Others: tetraethylbenzene, cumene, butylbenzene, diphenylethane, etc.

The benzene/ethylene feeding molar ratio was 2.9, and at the inlet of the catalyst layer, ethylene was not completely dissolved in benzene and ethylene bubbles were present.

When the β zeolite was used as a catalyst, the conversion of ethylene was 99.3%, namely, ethylene was substantially completely converted, and the selectivity of nuclear ethylation products was as very high as 99.7%. Moreover, these values were maintained for 30 Hr, namely, the activity was not deteriorated at all.

On the other hand, when the Y type zeolite was used as a catalyst, the selectivity of nuclear ethylation products was as very low as 95.5% and the conversion of ethylene was only 73% even in the early stages and fell down to 60% in only 4 hours of the reaction.

From the present comparative example, it can be seen that Y type zeolites widely used in conventional processes cannot be used at such a very low benzene/ethylene molar ratio as is employed in the present invention.

Comparative Example 2

The present comparative example was carried out for comparing reaction results obtained by employing different catalyst layer temperature profiles.

The same reaction apparatus as used in Comparative Example 1 was packed with 30 g of particles which had been prepared by grounding a shaped product of hydrogen ion type zeolite β catalyst obtained in the same manner as in Example 1, followed by classification and particle size regulation to 8 to 14 mesh. The catalyt packing region was a region between heights of 320 mm and 510 mm from the bottom of the reactor, and a stainless-steel Dickson packing of 3 mmφ was packed over and under the catalyst layer. Benzene was fed at a feed rate of 319 g/Hr through the bottom of the reactor (the inlet of the preheating layer). The internal pressure of the reactor was adjusted to 13.8 kg/cm$^2$G with the pressure control valve at the outlet of the reactor to make the inside of the system completely liquid-sealed. A heating medium at 230° C. was circulated in the heating medium jacket provided as heating layer, to adjust the temperature of the catalyst layer at its inlet to 195° C. Then, like benzene, ethylene was fed through the bottom of the reactor at a feed rate of 1.4 mol/Hr to initiate the reaction. The maximum attained temperature of the catalyst layer reached 232° C. in the middle region of the catalyst layer, but since partial evaporation was caused under the reaction conditions employed in the present comparative example, a further temperature rise was inhibited and the temperature of 232° C. was maintained also in the upper part of the catalyst layer. As in Comparative Example 1, a condenser was provided at the outlet of the reactor and the whole products were recovered as a liquid, which was analyzed by a gas chromatography. Table 6 shows the results of evaluating the reaction.

TABLE 6

| Catalyst | | H-β | |
|---|---|---|---|
| Packing amount (g) | | 30 | |
| Feed of materials | Benzene | 4.09 | |
| | Ethylene (mol/H) | 1.41 | |
| | BZ/EY molar ratio | 2.91 | |
| Reaction time (Hr) | | 10 | 30 |
| Temperature | Inlet of catalyst layer | 195 | 195 |
| | Exit end of catalyst layer (° C.) | 233 | 232 |
| Composition of solution | Benzene | 63.43 | 64.23 |
| | Ethylbenzene | 29.16 | 28.71 |
| | Diethylbenzene | 6.33 | 6.08 |
| | Triethylbenzene | 0.73 | 0.67 |
| | Others * | 0.36 | 0.32 |
| Benzene ring/ethyl group molar ratio | | 2.95 | 3.03 |
| Selectivity of nuclear ethylation (%) | | 99.34 | 99.38 |
| Convertion of ethylene (%) | | 98.3 | 95.6 |

Others: tetraethylbenzene, cumene, butylbenzene, diphenylethane, etc.

As described in Comparative Example 1, when the temperature of the catalyst layer at its inlet was adjusted to 135° C., the conversion of ethylene was 99.3%, namely, ethylene was substantially completely converted, and the selectivity of nuclear ethylation products was as very high as 99.7%. Moreover, these values were maintained for 30 Hr, namely, the activity was not deteriorated at all. On the other hand, the following became apparent: when as in the present comparative example, the temperature of the catalyst layer at its inlet was 195° C. which was remarkably out of the temperature range specified in the present invention, i.e., the temperature range of 50° C. or more lower than the maximum attained temperature of the catalyst layer, the conversion of ethylene was 98% even in the early stages, namely, ethylene was not completely converted; the selectivity of nuclear ethylation was as low as 99.3%; and moreover the deterioration of the catalytic activity was relatively rapid. When the industrial production of ethylbenzene is considered, such a catalyst layer temperature profile is not preferable because it extremely increases the flow rate (recycling rate) of the evaporation gas and hence decreases the recovery rate of the product solution.

INDUSTRIAL APPLICABILITY

According to the present invention, alkylation of benzene can be carried out at a very low benzene/ethylene feeding molar ratio without decreasingthe catalytic activity, while maintaining a very high selectivity of nuclear ethylation and complete conversion of ethylene. Furthermore, the reaction can be carried out with a simple apparatus under a low pressure. In addition, since complete dissolution of ethylene is not necessary unlike in conventional processes, the reaction can be carried out using starting ethylene of low purity. These facts are very advantageous for the industrial production of ethyl-benzene.

Relation to Other Applications

The present application is based on Japanese Patent Application No. 08-207567 filed on Jul. 19, 1996 and the contents thereof are incorporated as a whole into the present specification by reference.

We claim:

1. A process for producing ethylated benzene by a reaction of benzene with ethylene in the presence of a catalyst containing a zeolite β by using a fixed-bed ascending-flow reactor, which comprises a) carrying out the reaction under conditions under which ethylene bubbles are present at the inlet of a catalyst layer when ethylene is fed upward from under the catalyst layer, b) recovering reaction products as a liquid from the upper part of the reactor and at the same time taking out a distillate composed mainly of unreacted benzene therefrom as vapor, and c) adjusting the temperature of the catalyst layer at its inlet to a temperature at least 50° C. lower than the maximum attained temperature of the catalyst layer.

2. A process for producing ethylated benzene according to claim 1, wherein the feeding molar ratio of benzene to ethylene is 1 to 6.

3. A process for producing ethylated benzene according to claim 1, wherein the benzene ring/ethyl group molar ratio of the product solution obtained is 1 to 3.

4. A process for producing ethylated benzene according to claim 1, which employs such a catalyst layer temperature profile that the temperature of the catalyst layer at its inlet is 30–200° C. and the maximum attained temperature of the catalyst layer is 170–250° C.

5. A process for producing ethylated benzene according to claim 1, wherein the partial pressure of the distillate taken out as vapor from the upper part of the reactor is 5 to 20 kg/cm²G.

6. A process for producing ethylated benzene according to claim 1, wherein the distillate composed mainly of unreacted benzene which is recovered as vapor from the reactor is recycled and fed to the reactor.

7. A process for producing ethylated benzene according to claim 6, wherein the feeding molar ratio of benzene to ethylene is 1 to 3.

* * * * *